United States Patent
Johnsen et al.

(10) Patent No.: US 12,161,298 B2
(45) Date of Patent: Dec. 10, 2024

(54) SAMPLING DEVICE FOR THE USE WITH AN ENDOSCOPE

(71) Applicant: AMBU A/S, Ballerup (DK)

(72) Inventors: Lasse Markworth Johnsen, Birkerød (DK); Jesper Mads Bartroff Frederiksen, Vedbæk (DK); Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 1191 days.

(21) Appl. No.: 16/610,362

(22) PCT Filed: May 2, 2018

(86) PCT No.: PCT/DK2018/050087
§ 371 (c)(1),
(2) Date: Nov. 1, 2019

(87) PCT Pub. No.: WO2018/202266
PCT Pub. Date: Nov. 8, 2018

(65) Prior Publication Data
US 2022/0338846 A1    Oct. 27, 2022

(30) Foreign Application Priority Data
May 2, 2017    (DK) .......................... PA 2017 70293

(51) Int. Cl.
*A61B 1/015*   (2006.01)
*A61B 1/00*    (2006.01)
(Continued)

(52) U.S. Cl.
CPC .......... *A61B 1/015* (2013.01); *A61B 1/00066* (2013.01); *A61B 1/00128* (2013.01);
(Continued)

(58) Field of Classification Search
CPC ............ A61B 1/00094; A61B 1/00112; A61B 1/00119; A61B 1/00121; A61B 1/00128;
(Continued)

(56) References Cited

U.S. PATENT DOCUMENTS

| 4,643,197 A | 2/1987 | Greene et al. |
| 4,870,975 A | 10/1989 | Cronk et al. |

(Continued)

FOREIGN PATENT DOCUMENTS

| CN | 102271590 | 12/2011 |
| CN | 103153199 | 6/2013 |

(Continued)

OTHER PUBLICATIONS

Global dossier translation of notification of grant from CN application No. 201880028621.7, mailed Feb. 9, 2022, 2 pgs.
(Continued)

*Primary Examiner* — Ryan N Henderson
(74) *Attorney, Agent, or Firm* — Faegre Drinker Biddle & Reath LLP

(57) ABSTRACT

A sampling device (9) for the use with an endoscope (1) having a suction channel and a suction connector (4) in communication with said suction channel. The sampling device (9) is adapted for connection to the suction connector (4) and said sampling device (9) is adapted for connection to a vacuum source. The sampling device (9) is adapted for forming a rigid connection with said endoscope (1) when connected to the suction connector thereof (4).

26 Claims, 11 Drawing Sheets

(51) Int. Cl.
*A61B 10/00* (2006.01)
*A61B 10/04* (2006.01)

(52) U.S. Cl.
CPC ...... *A61B 1/00131* (2013.01); *A61B 10/0045* (2013.01); *A61B 10/0096* (2013.01); *A61B 10/04* (2013.01)

(58) Field of Classification Search
CPC ....... A61B 1/00131; A61B 1/015; A61B 1/12; A61B 1/126; A61B 1/127; A61B 2017/005; A61B 10/04; A61B 10/0045; A61B 10/0096; A61M 1/60; A61M 1/64
See application file for complete search history.

(56) References Cited

U.S. PATENT DOCUMENTS

| | | | |
|---|---|---|---|
| 4,909,782 A | 3/1990 | Semm et al. | |
| 4,922,902 A | 5/1990 | Wuchinich et al. | |
| 4,957,492 A * | 9/1990 | McVay | A61M 1/79 604/405 |
| 5,290,303 A | 3/1994 | Pingleton et al. | |
| 5,334,183 A | 8/1994 | Wuchinich | |
| 5,347,991 A | 9/1994 | Nakao et al. | |
| 5,363,860 A | 11/1994 | Nakao et al. | |
| 5,409,013 A | 4/1995 | Clement | |
| 5,624,418 A * | 4/1997 | Shepard | A61M 1/79 210/85 |
| 6,110,127 A * | 8/2000 | Suzuki | A61B 10/06 606/205 |
| 6,190,330 B1 | 2/2001 | Harhen | |
| 6,331,165 B1 | 12/2001 | Turturro et al. | |
| 6,375,625 B1 | 4/2002 | French et al. | |
| 6,632,182 B1 | 10/2003 | Treat | |
| 6,840,909 B2 | 1/2005 | Gatto | |
| 6,852,108 B2 | 2/2005 | Barry et al. | |
| 7,172,579 B2 | 2/2007 | Barzell et al. | |
| 7,708,938 B2 | 5/2010 | Mariotti et al. | |
| 7,806,835 B2 | 10/2010 | Hibner et al. | |
| 7,963,910 B2 * | 6/2011 | Okada | A61B 10/06 600/156 |
| 8,070,756 B2 * | 12/2011 | Secrest | A61B 17/3421 606/115 |
| 8,088,079 B2 * | 1/2012 | Kaye | A61B 10/0283 600/562 |
| 8,262,565 B2 * | 9/2012 | Okada | A61B 1/018 606/115 |
| 8,303,489 B2 * | 11/2012 | Ito | A61B 1/015 604/319 |
| 8,382,660 B2 * | 2/2013 | Okada | A61B 10/0096 600/156 |
| 8,460,182 B2 | 6/2013 | Ouyang et al. | |
| 8,974,399 B2 | 3/2015 | Teixeira et al. | |
| 9,204,868 B2 | 12/2015 | Furlong et al. | |
| 9,332,969 B2 | 6/2016 | Han et al. | |
| 9,408,593 B2 | 8/2016 | Furlong et al. | |
| 9,421,001 B2 | 8/2016 | Speeg et al. | |
| 9,486,185 B2 | 11/2016 | Hibner | |
| 9,486,186 B2 | 11/2016 | Fiebig et al. | |
| 9,498,193 B2 | 11/2016 | Smith et al. | |
| 9,538,994 B2 | 1/2017 | Hibner et al. | |
| 9,545,244 B2 * | 1/2017 | Parihar | A61B 10/0096 |
| 9,603,587 B2 | 3/2017 | Fiebig et al. | |
| 9,713,461 B2 * | 7/2017 | Mikkaichi | A61B 10/0283 |
| 9,737,285 B2 | 8/2017 | Fiebig et al. | |
| 9,943,291 B2 * | 4/2018 | VanderWoude | A61M 1/72 |
| 9,968,242 B2 * | 5/2018 | Salman | A61B 1/015 |
| 10,441,206 B2 * | 10/2019 | Locke | A61B 10/0096 |
| 10,667,735 B2 * | 6/2020 | Locke | A61B 10/0045 |
| 11,696,748 B2 | 7/2023 | Johnsen et al. | |
| 2004/0068291 A1 | 4/2004 | Suzuki | |
| 2006/0235433 A1 * | 10/2006 | Secrest | A61B 17/32056 606/114 |
| 2006/0287579 A1 * | 12/2006 | Okada | A61B 10/06 600/156 |
| 2007/0088199 A1 * | 4/2007 | Ito | A61B 1/00137 600/156 |
| 2007/0179341 A1 * | 8/2007 | Okada | A61B 1/018 600/156 |
| 2007/0191731 A1 * | 8/2007 | Kaye | A61B 10/0283 600/565 |
| 2007/0213632 A1 | 9/2007 | Okazaki et al. | |
| 2008/0082021 A1 | 4/2008 | Ichikawa | |
| 2008/0163669 A1 | 7/2008 | Gregory et al. | |
| 2008/0183037 A1 | 7/2008 | Ichikawa et al. | |
| 2009/0234192 A1 * | 9/2009 | Okada | A61B 10/0096 600/156 |
| 2010/0174210 A1 | 7/2010 | Han et al. | |
| 2012/0095369 A1 * | 4/2012 | Teixeira | A61M 1/77 600/573 |
| 2013/0123663 A1 | 5/2013 | Hibner et al. | |
| 2013/0144186 A1 | 6/2013 | Furlong | |
| 2014/0081170 A1 * | 3/2014 | Parihar | A61B 10/0096 600/567 |
| 2014/0088460 A1 | 3/2014 | Teixeira | |
| 2014/0378864 A1 | 12/2014 | Hibner | |
| 2015/0209491 A1 | 7/2015 | Cushner et al. | |
| 2016/0166239 A1 * | 6/2016 | Mikkaichi | A61B 1/015 600/573 |
| 2016/0256139 A1 * | 9/2016 | Hadley | A61B 1/015 |
| 2019/0038195 A1 | 2/2019 | Peterson et al. | |
| 2019/0054217 A1 | 2/2019 | Axon | |
| 2020/0121304 A1 | 4/2020 | Johnsen et al. | |
| 2020/0188921 A1 | 6/2020 | Goodman | |
| 2023/0320708 A1 | 10/2023 | Johnsen et al. | |

FOREIGN PATENT DOCUMENTS

| | | |
|---|---|---|
| EP | 1908391 A1 | 4/2008 |
| EP | 2 100 550 | 1/2011 |
| EP | 1 813 184 | 1/2016 |
| WO | WO 99/08731 | 2/1999 |
| WO | WO 2006/039646 | 4/2006 |
| WO | 2008/144515 A1 | 11/2008 |
| WO | WO 2012/051545 | 4/2012 |
| WO | 2014/028366 A1 | 2/2014 |
| WO | 2015/031217 A1 | 3/2015 |
| WO | 2016/196536 A1 | 12/2016 |
| WO | 2017/075415 A1 | 5/2017 |
| WO | 2017/087411 A1 | 5/2017 |

OTHER PUBLICATIONS

Global dossier translation of office action from CN application No. 201880025464.4, mailed Dec. 28, 2021, 6 pgs.
Global dossier translation of office action from CN application No. 201880028621.7, mailed Jul. 30, 2021, 7 pgs.
International Search Report and Written Opinion from corresponding Application No. PCT/DK2018/050086, dated Aug. 22, 2018.
First Office Action issued in CN201880028621.7, dated Jul. 30, 2021, with informal translation.
Examination Report issued in EP18722888.7, dated Jan. 13, 2021, 5 pages.
International Search Report and Written Opinion from corresponding Application No. PCT/DK2018/050087, dated Jul. 3, 2018.
Danish Search Report from corresponding Application No. PA 2017 70293, dated Jun. 20, 2017.

* cited by examiner

SAMPLING DEVICE FOR THE USE WITH AN ENDOSCOPE

CROSS-REFERENCE TO RELATED APPLICATIONS

This application is a National stage application filed under 35 U.S.C. § 371 of International Application No. PCT/DK2018/050087, filed on May 2, 2018, which claims the benefit of Denmark Patent Application No. PA 2017 70293, filed on May 2, 2017, which applications are incorporated herein by reference in their entirety.

TECHNICAL FIELD

The present invention relates to a sampling device for the use with an endoscope having a suction channel and a suction connector in communication with said suction channel, in particular a sampling device being adapted for connection to the suction connector and said sampling device being adapted for connection to a vacuum source.

BACKGROUND

Such sampling devices are inter alia used in procedures such as bronchial lavage (BL), bronchial wash (BW) or bronchoalveolar lavage (BAL) which are commonly used procedures for obtaining samples of organic material from a lung segment of a patient. This is basically done by flushing a lung segment with sterile water, normally a sterile aqueous saline solution, and then sucking the water into a sample container. More specifically the distal end of an endoscope is advanced to the location in the lung where the sample is to be taken. In bronchoalveolar lavage, the distal end is then pressed into firm engagement against the interior of the lung to help securing the position in a process commonly referred to as wedging.

Via the working channel of the endoscope, sterile water, e.g. a 0.9% saline solution, or isotonic saline, is instilled into the lung at the sample location and as much as possible extracted again, now containing organic material, and thus constituting a sample. Typically, this is done by attaching a filled syringe of a volume between 20 ml and 60 ml, e.g. 50 ml to the working channel of the endoscope, via a communication port in endoscope handle. The syringe is then used for each instillation as well as the subsequent extraction. This process is normally repeated several times in a row with new syringes, e.g. three to four, the samples being suitable for various purposes, depending which number of sample in the sequence they are, because the composition of the organic material varies. If the syringe is used for extraction, the sample would be transferred to a sample container suitable for securing biological material. Upon extraction the sample containers are therefore normally labelled accordingly.

As an alternative to the extraction using the syringe, the extraction may be performed using an external suction and a Lukens trap, e.g. as disclosed in U.S. Pat. No. 4,643,197.

Using a Lukens trap attached to the endoscope in the manner disclosed in U.S. Pat. No. 4,643,197, i.e. interposed in the flexible suction line leading from the endoscope to the vacuum or suction source (the two terms are considered to be synonyms throughout this description), involves several disadvantages when carrying out the procedure. One such disadvantage is that being suspended on the line the operator has only little sense of and attention to the orientation of the trap, as the operators visual focus is on the monitor the major part of the attention is on other part of the procedure e.g. the delicate parts of the procedure within the patient. It therefore does happen that the Lukens trap inadvertently ends up in an orientation where the sample is lost, because it gets sucked out of the trap by the vacuum source or suction. Another disadvantage is that there is a lot of work involved in connecting and disconnecting tubes as well as other parts, if e.g. the operator needs to change between obtaining a sample and suction in order to clean without sampling.

SUMMARY OF DISCLOSED EMBODIMENTS

Based on this, it is the object of the present invention to provide a sampling device which renders itself for the use with an endoscope and which does not suffer from the above drawbacks.

According to a first aspect of the invention this object is achieved by a sampling device according to the opening paragraph, in which the sampling device is adapted to be interposed between the suction connector of the endoscope and the vacuum source and for forming a rigid connection with said endoscope when connected to the suction connector thereof.

Forming a rigid connection between the endoscope and the sampling device links the orientation of the sampling device to that of the endoscope. This, in turn, gives the operator a much more immediate and instinctive sense of the orientation of the sampling device, because the orientation follows that of the endoscope, the handle of which the operator has a firm grip.

According to a second aspect of the invention, the object is achieved by a sampling system for the use with an endoscope, said sampling system comprising a sampling device and a sampling container adapted for attachment to said sampling device.

According to a third aspect of the invention the object is achieved by a method for performing a lavage comprising the steps of providing an endoscope, providing a sampling device according to the first aspect of the invention, attaching the sampling device to the endoscope, connecting the sampling device to a vacuum source, inserting an insertion part of the endoscope into a body cavity, administering a saline solution through the endoscope to the body cavity, collecting a sample by drawing fluid from the body cavity through the endoscope and the sampling device.

According to a fourth aspect of the invention, the object is achieved by providing a kit comprising a sampling device according to the first aspect of the invention a saline cartridge or a syringe for saline, at least one sample container.

According to a first preferred embodiment of the sampling device according to the first aspect of the present invention, the sampling device comprises a socket defining an insertion direction adapted to receive the suction connector of the endoscope in said insertion direction for forming said rigid connection, and the sampling device is furthermore adapted to engage the endoscope in a manner preventing rotation around the suction connector. Thereby the good sense of orientation is maintained at all angles.

According to a second preferred embodiment, the sampling device comprises a male connector defining an insertion direction adapted to engage a suction connector socket of the endoscope in said insertion direction for forming said rigid connection, and the sampling device is furthermore adapted to engage the endoscope in a manner preventing rotation around the suction connector. This allows the sampling device to be used with existing endoscopes of the kind provided with a socket or a receptacle, i.e. a female connector, rather than a male connector.

According to a further preferred embodiment the sampling device comprises a valve, preferably shunt valve or a three-way valve for diverting the suction through the sampling device through a sample container. Thus, only when sampling is needed is the suction diverted through the sample container. When not the flow may be shunted around the sample container, allowing the endoscope to be used independently of the attached sampling device, i.e. as if it was not there.

According to a preferred embodiment, the valve actuator is adapted to be operated using a single finger of a hand of the operator and is located in a position on said sampling device which, in the mounted position of the endoscope is accessible and operable by the finger of the hand of an operator with which the operator is gripping the endoscope. This allows the valve actuator to be operated by the operator himself without having to release the grip on the endoscope and removing the hand from the handle, using another hand or relying on additional personnel. This, in turn, facilitates the procedure and keeps number of personnel involved down.

According to another preferred embodiment, the sampling device comprises a sample container connector adapted for connecting a sample container. This allows the sample container to be easily attached, removed, and replaced during the sampling procedure.

According to yet another preferred embodiment, the sample container connector extends in a direction parallel to or coincident with said insertion direction. When, as is the case for many endoscopes, the suction connector extends laterally, i.e. in a direction transverse to the insertion tube insertion direction of the endoscope as defined by the insertion tube thereof (not to be confused with the insertion direction of the connector), this allows the forces applied to be transverse to the insertion direction. This, in turn reduces the risk of undesired translatory motion of the insertion tube of the endoscope within the patient.

According to a further preferred embodiment the sample container connector is adapted to penetrate at least one seal of the sample container. This allows automatic sealing of the sample container upon removal, and thus a reduced risk of spilling the sample or of contaminating it.

According to yet a further preferred embodiment, the sampling device is adapted for single use. This allows the sampling device to be constructed from low cost materials such as plastics, because it needs not be able to withstand the harsh circumstances of cleaning and sterilization, such as the high temperatures of an autoclave.

BRIEF DESCRIPTION OF THE DRAWINGS

The invention will now be described in greater detail based on non-limiting exemplary embodiments, and with reference to the drawings on which.

DETAILED DESCRIPTION

Figure 1:
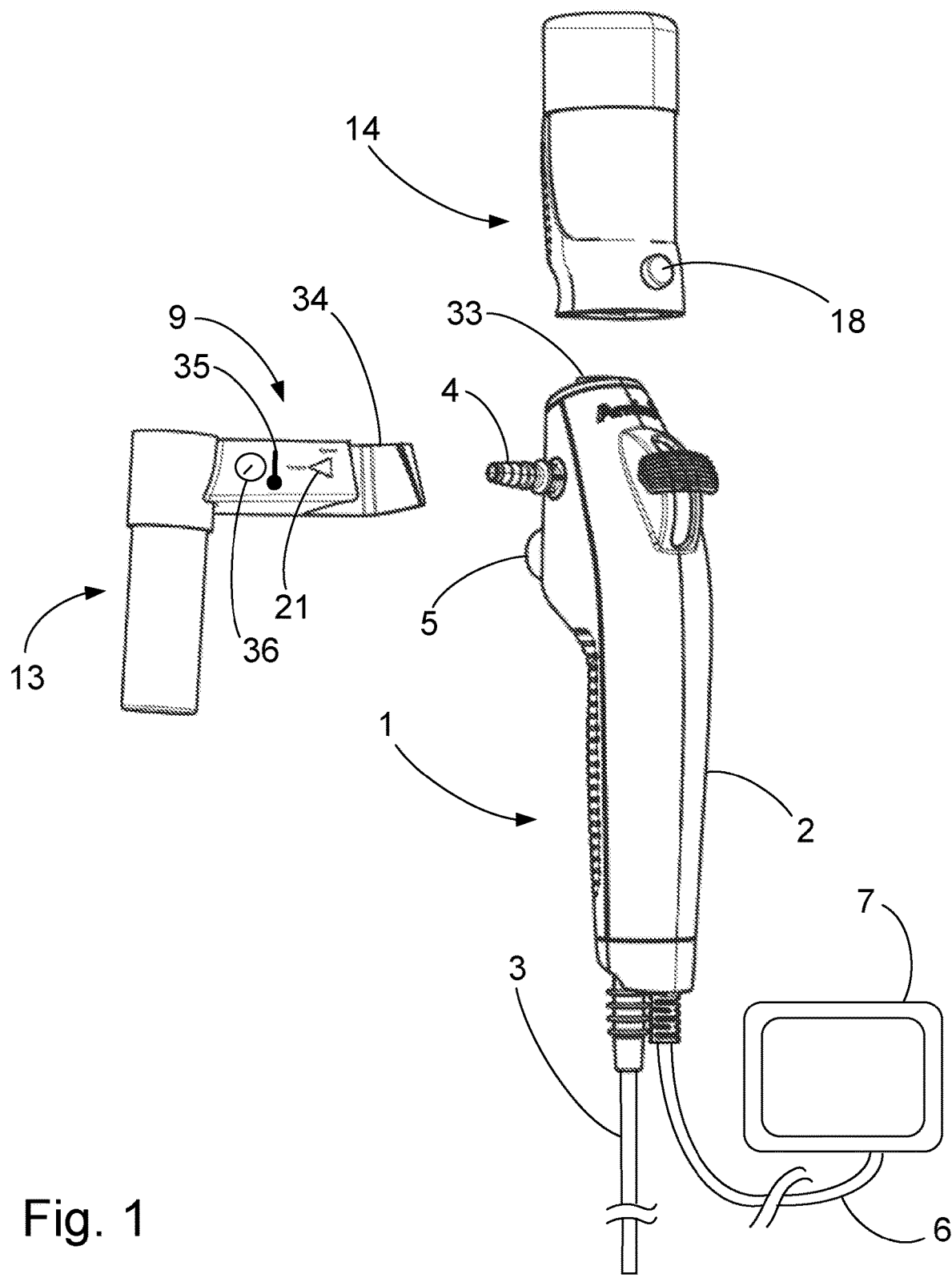
FIG. 1 shows an exploded view of a sampling system comprising an endoscope, a saline cartridge, a sampling device according to the invention, and a sample container.

Turning first to FIG. 1 an endoscope 1 having a handle 2 and an insertion tube 3 is shown. For illustration purposes, the insertion tube 3 is only shown in part in FIG. 1 and omitted entirely in the remainder of the figures. For the purposes of this description the insertion tube 3 defines a longitudinal direction of the endoscope 1. At the distal end of the insertion tube 3 an articulated bending section allowing the insertion tube to be maneuvered trough the body cavities. In the present description where the outset is bronchial or bronchoalveolar lavage, such body cavities would include trachea and bronchi of the patient, but as will be appreciated by the skilled person the use of the sampling device according to the present invention is not limited to these procedures. The distal tip of the bending section comprises openings connected to one or more channels at least one of which, such as the working channel 19, may be used as a suction channel. The suction channel may be connected to a suction or vacuum source at a connector 4 by the activation of a valve operated by a push-button 5 on the handle 2 of the endoscope 1 in a well-known manner. The distal tip furthermore includes a light source and a camera connected via a cable 6 to a monitor 7 allowing the operator and others to monitor the actions performed within the patient.

The connector 4 is of a standard type for attaching a flexible suction tube 8, in turn connected to a vacuum or suction source, e.g. the wall suction normally found in hospitals. The connector 4 is generally tubular male connector with a taper to allow easy connection of the flexible suction tube 8 and with circumferential corrugations or barbs allowing a secure connection of the flexible suction tube 8 in a well-known manner. The connector 4 need not be an integral part of the endoscope 1. In some multiple use endoscopes 1 the connector is a separate interchangeable part. Furthermore, in some existing endoscopes 1 the connector is a receptacle or a socket, i.e. a female connector.

Figure 2:
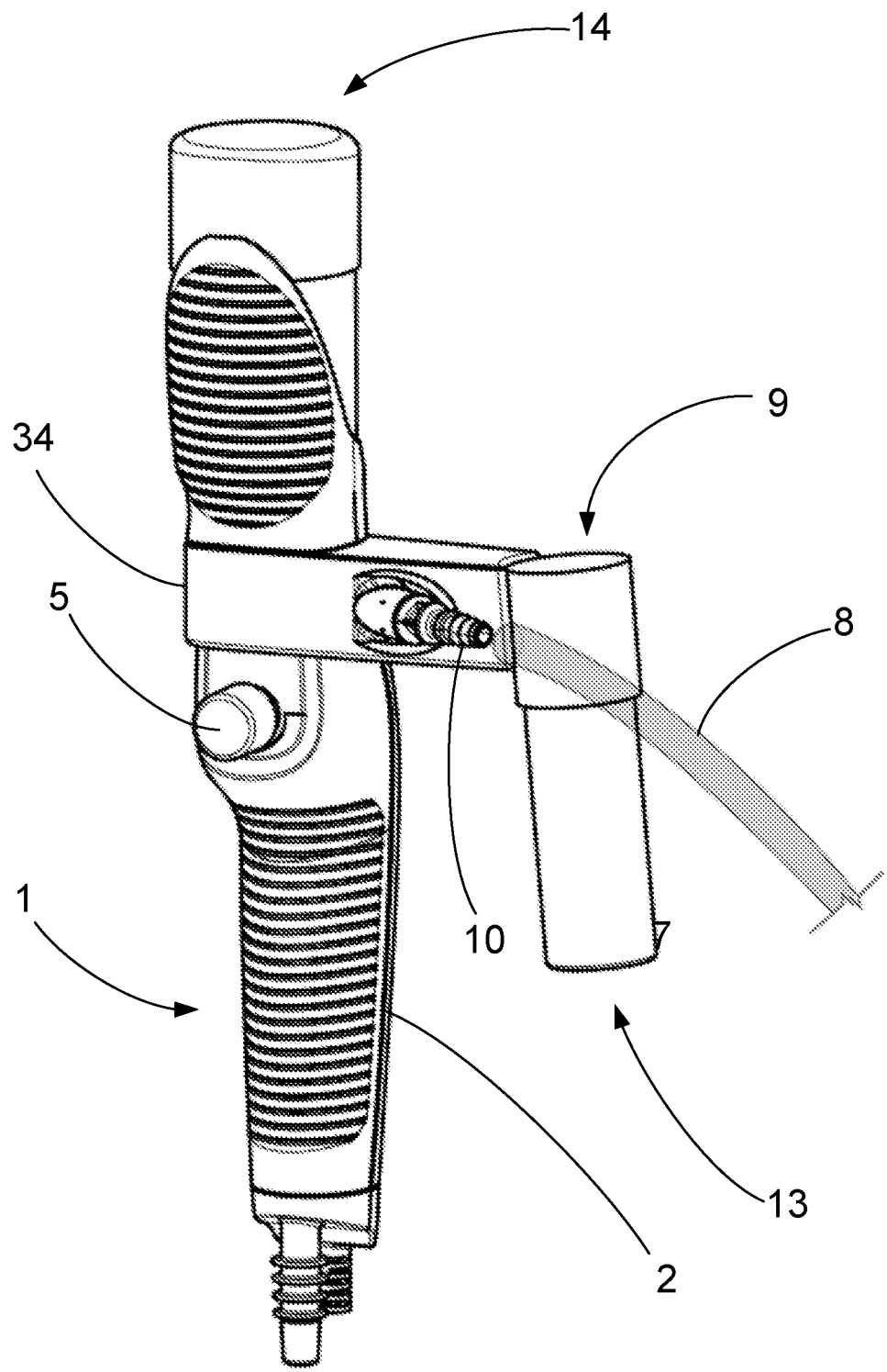
FIG. 2 shows the sampling system of FIG. 1 in an assembled state.

However, rather than connecting the flexible suction tube 8 directly to the connector 4, the sampling device 9 according to the invention may be connected to the connector 4. The sampling device 9, in turn, may then be connected to the flexible suction tube 8. The sampling device 9 is thus to be interposed between the suction connector of the endoscope 1 and the vacuum source. For this the sampling device 9 has an identical, similar or at least corresponding connector 10 to which the flexible suction tube 8 may be attached, as indicated in FIG. 2, and a receptacle 28 (not visible in FIGS. 1-3, but in FIG. 10) acting as a socket for receiving and rigidly securing the connector 4. Evidently, if the connector 4 is a separate interchangeable part as mentioned above, the sampling device could be adapted to fit directly in the endoscope 1, so as to entirely avoid the connector. How exactly this connection is achieved is of less importance, the essence is that the endoscope 1 and the sampling device 9 are mutually connectable, irrespective of whether the endoscope 1 or the device 9 carries the male or female part, and irrespective of whether there is an interposed interchangeable part. To make the sampling device 9 more versatile, and allow it to be used with a wide range of endoscopes 1, it is furthermore envisaged that in some embodiments the sampling device 9 comprises the actuator, such as a push-button 5, for the activation of a valve 22 for activating suction through the sampling device 9. In such embodiments the actuator is preferably located so that it is easily accessible by the operator, possibly by a finger of the hand holding the handle 2 of the endoscope 1.

Figure 3:
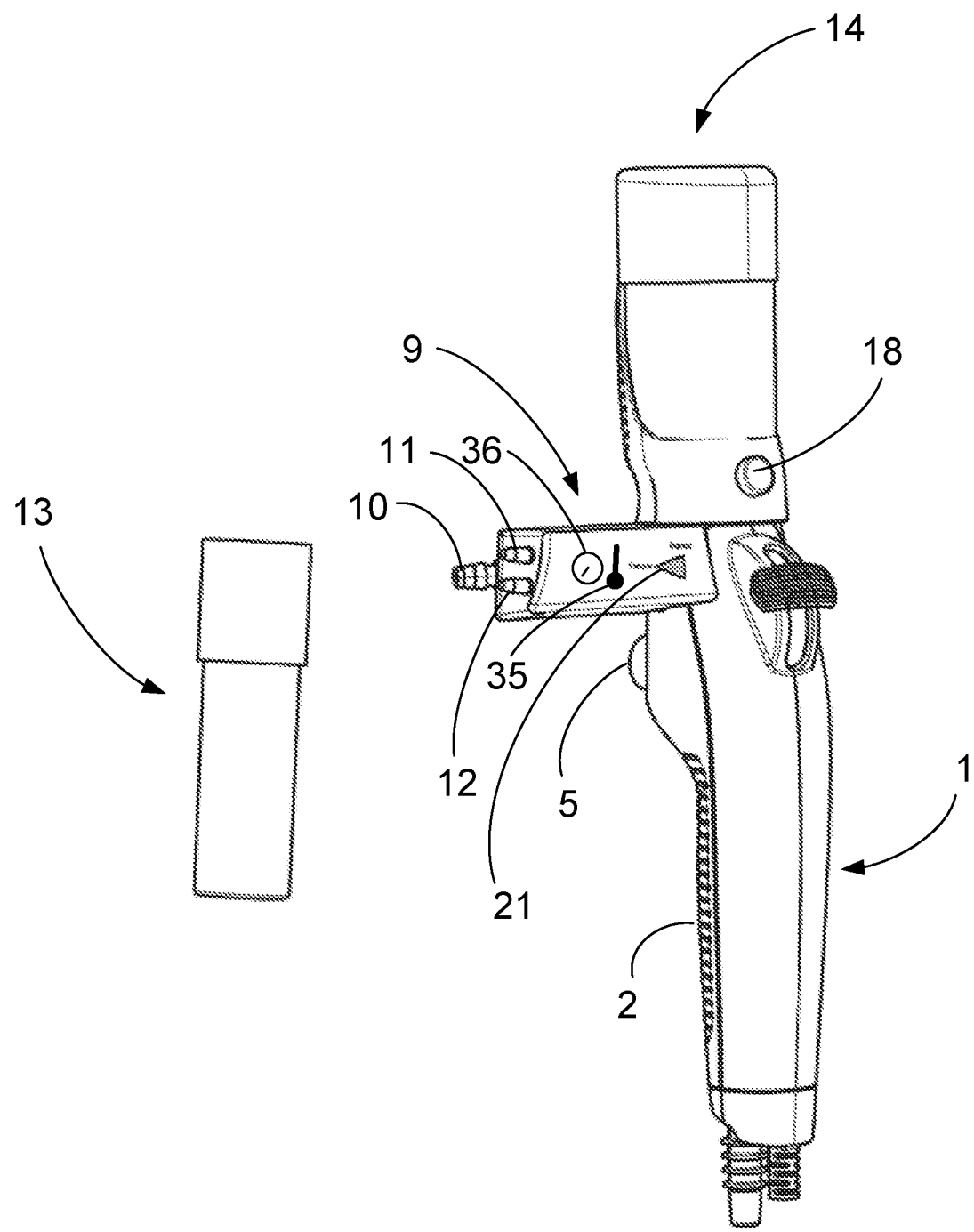
FIG. 3 shows the sampling system of FIG. 1 in an assembled state, but with an interchangeable sample container detached.

Apart from having a receptacle 28 for receiving the connector 4, the sampling device 9 furthermore comprises a sample container connector comprising a pair of tubular protrusions 11, 12 adapted to engage and be inserted through the wall of a preferably detachable sample container 13, preferable through openings covered by a membrane. Using a pair of tubular protrusion 11, 12 allow the easy penetration of a suitable sealing, such as lip seals, on the sample container 13. FIG. 3 shows a detachable sample container 13 in a situation where it is detached from the sampling device 9. Preferably, the sample container is adapted to self-seal the openings through which the tubular protrusions 11, 12 passes, when the protrusions are not present in the openings, i.e. when the sample container 13 is detached from the sampling device 9. I.e. the membrane seals the aperture or slit when protrusions are not present, and when the protrusions are present the membrane seals tightly around the protrusions. This allows the extraction of several samples one after the other by simple removal and replacement of the filled sample container 13 with a new and empty one. Since the sample container 13 self-seals, the risk of contamination of not only the sample in the container but also the surroundings, e.g. personnel, is minimal. The handling of the samples is thus facilitated, as the personnel needs to care less about contamination. This allows the personnel to focus their attention on other parts of the procedure, in turn, facilitating the overall procedure.

The tubular protrusions 11, 12 are preferably arranged in such a manner on the sampling device 9 that when the sampling device 9 is correctly attached to the endoscope 1 with the connector 4 in the receptacle 28 of the sampling device 9, the tubular protrusions 11, 12 extend in a direction transversely to the longitudinal direction of the endoscope 1. In this illustrated embodiment where the connector 4 extends itself transversely to the longitudinal direction of the endoscope, this means that the tubular protrusions 11, 12 of the sample container connector extend in parallel with the receptacle 28 and consequently in parallel with the connector 4 of the endoscope 1, i.e. in parallel with the insertion direction or possibly even coincident therewith. This has the advantage that displacements, such as jerks when detaching or attaching the sample container 13 will mainly be in the transverse direction to the endoscope 1 and therefore be less likely to cause any displacement of the endoscope in the longitudinal direction, i.e. the aforementioned endoscope insertion direction. Such longitudinal displacement is undesired as the displacement could cause the tip of the endoscope to move within the patient, which could result in loss of the wedge position and thereby extend the time for the procedure.

Turning now to FIG. 1 again, an optional third separate part of the system in the form of a saline cartridge 14, adapted to be attached to the endoscope 1 in fluid connection with a working channel 19 thereof via an inlet port 33, is shown. The saline cartridge is a canister pre-filled with a saline solution and with pressurization means for exerting pressure on the saline solution. The pressurization means may be a releasable piston 15 biased to expel the saline solution by means of a suitable biasing means, such as a spring 16, as best seen in the schematic drawings of FIGS. 4 and 5. Other pressurization means such as compressed air, e.g. in a bladder within the saline cartridge 14, would of course also be possible. When the biasing means acts on the saline solution to expel it, the operator may control the volume of liquid expelled by means of a valve 17 actuated via a push-button 18 arranged in a suitable location on the saline cartridge 14. With the saline cartridge 14 in proper position and in fluid connection with the working channel 19, the expelled liquid would be dispensed into the working channel 19, and via the working channel instilled at the desired location in the patient at the tip of the endoscope 1. As can best be seen from FIG. 3 one such suitable location for the push-button 18 would be in close proximity to the connection point of the cartridge 14 to the working channel 19 of the endoscope, so as to have short fluid paths. Furthermore, this brings the push-button 18 close to the operator's fingers when the cartridge 14 is correctly attached to the endoscope 1, as illustrated in FIG. 3.

Having instilled the saline solution in the patient a liquid sample can now be extracted using the part of the system comprising the endoscope 1, the sampling device 9, the sample container 13 and the flexible suction tube 8 to the vacuum or suction source.

Figure 4:
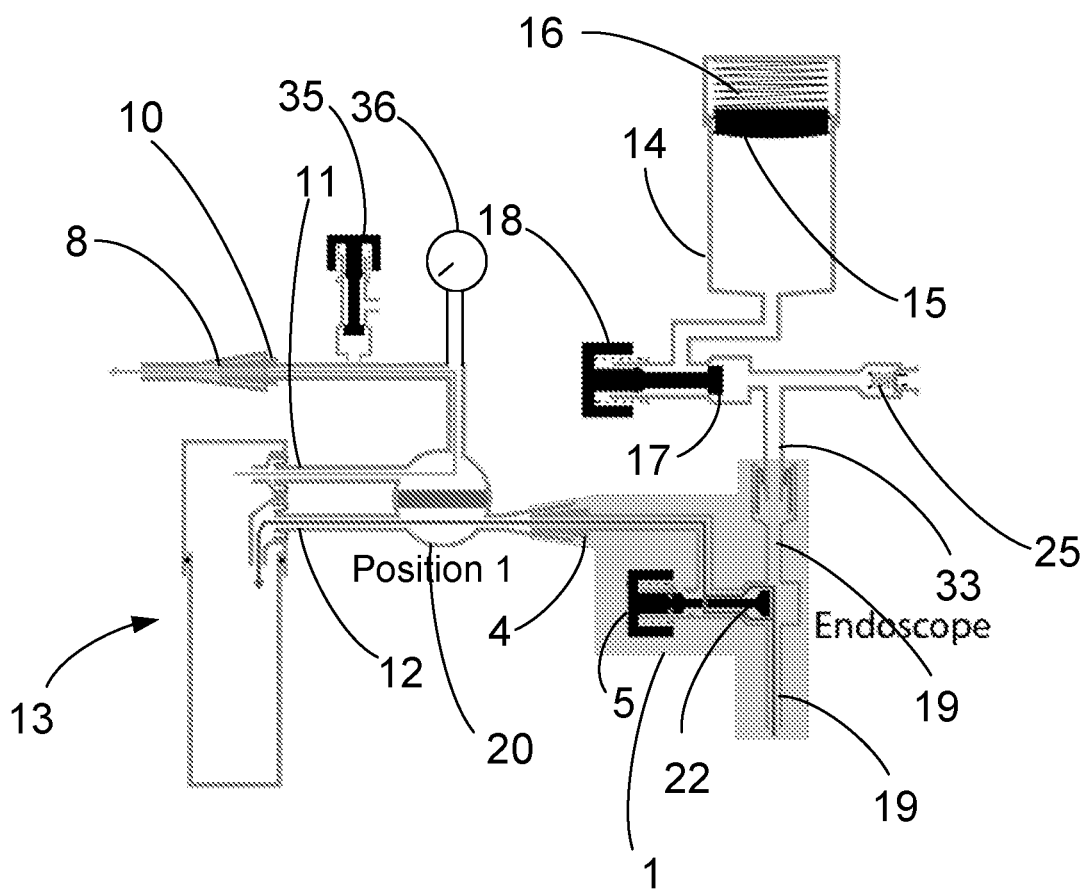
FIG. 4 shows a schematic diagram of the sampling system in the assembled state of FIG. 2 and in the sampling configuration.

To do so, the operator or another suitable person in the team turns a valve 20 via a valve actuator 21 such as a knob or the like to the position shown in FIG. 4 ("Position 1", also corresponding to "Position 1" in FIG. 7a), to establish a fluid passage from the tubular protrusion 12 through the sampling device 9. Preferably, the valve actuator 21 is located in a position on said sampling device which in the mounted position of the endoscope 1 is accessible by a hand of an operator with which the operator is gripping the handle 2 of the endoscope 1. Thus the valve actuator 21 is less than 30 mm away from the handle 2 of the endoscope 1, preferably less than 20 mm away. The valve actuator 21 may be located on a side of the sampling device 9 where it can be seen by the operator and operated by the thumb of the operator (See FIGS. 1, 3, 8 and 10-12). It is however, not excluded that it may be located elsewhere and operated by another finger, e.g. on the opposite side of what is shown in FIGS. 1, 3, 8 and 10-12, and operated with the index finger. In either case, the valve actuator 21 is adapted to be operated by a single finger of the operator. Since, like the endoscope 1 itself, the sampling device 9 is intended as a disposable device, i.e. single use device to be thrown away after the sampling procedure, it is easy to adapt the valve actuator 21 to be operable with a single finger. More specifically, the valve actuator may be provided with grooves between 37 and/or protrusions 38 allowing for good friction, because such grooves 37 and/or protrusions need not be cleaned and sterilized after use. Likewise, other friction enhancing features could be used, such as knurling and the like.

Figure 5:
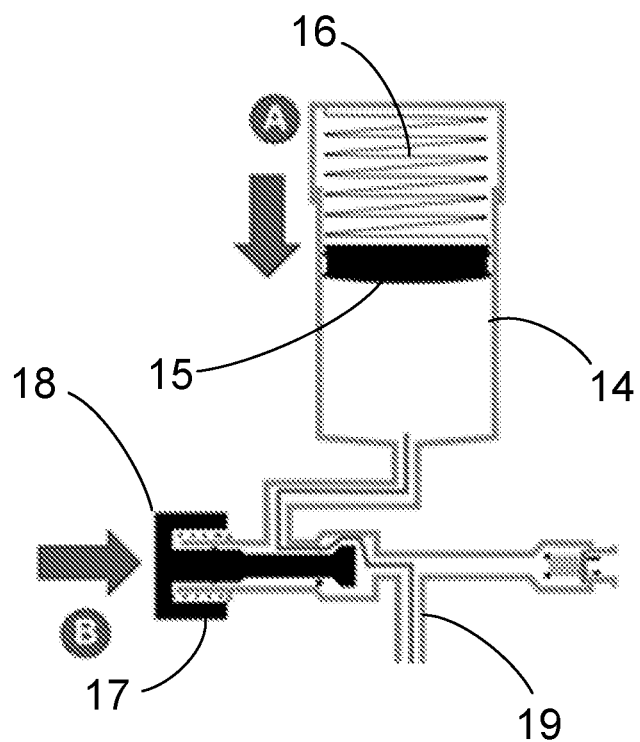
FIG. 5 shows a schematic diagram of the sampling system of FIG. 4 in the non-sampling position.
Figure 6:
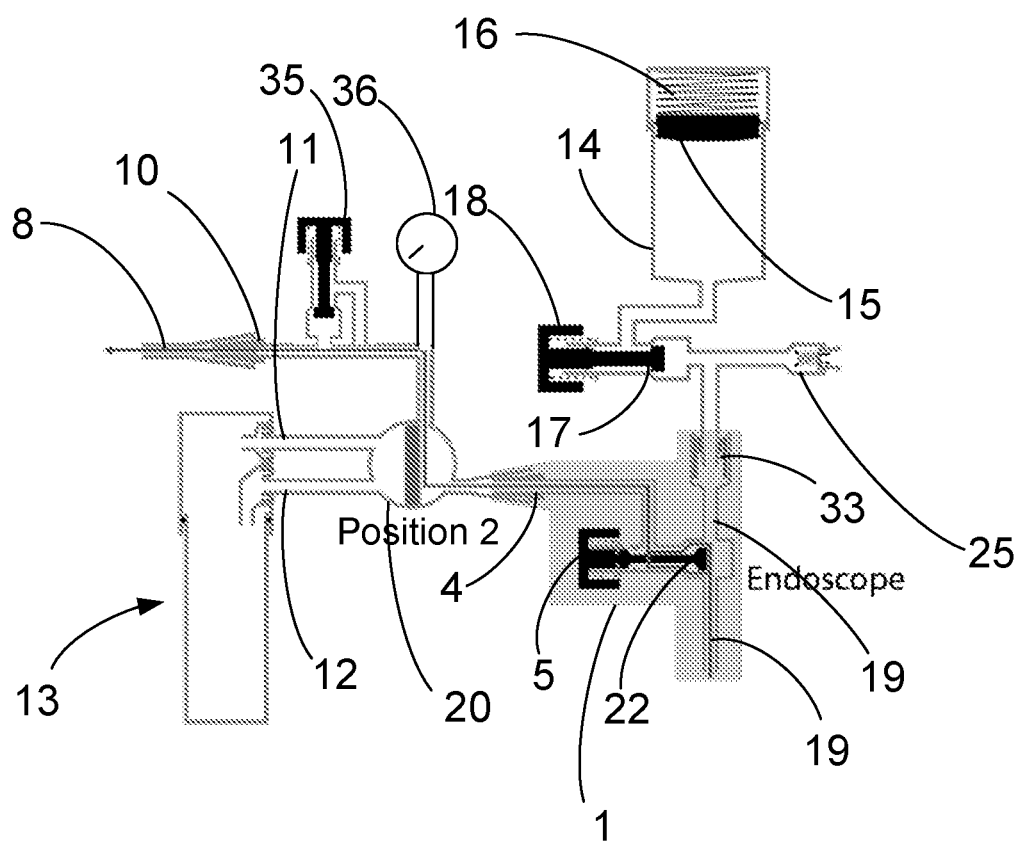
FIG. 6 shows a schematic diagram of the saline cartridge.
Figure 7A:
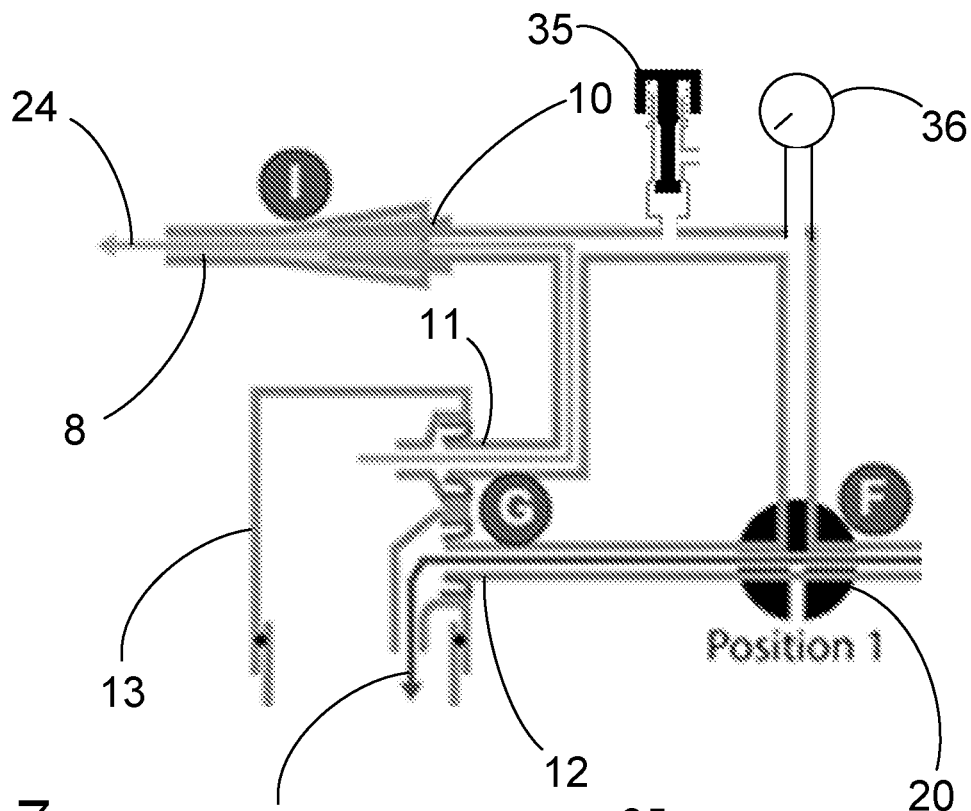
FIGS. 7a and 7b show various flow paths an alternative embodiment of the sampling device using a three-way valve.
Figure 7B:
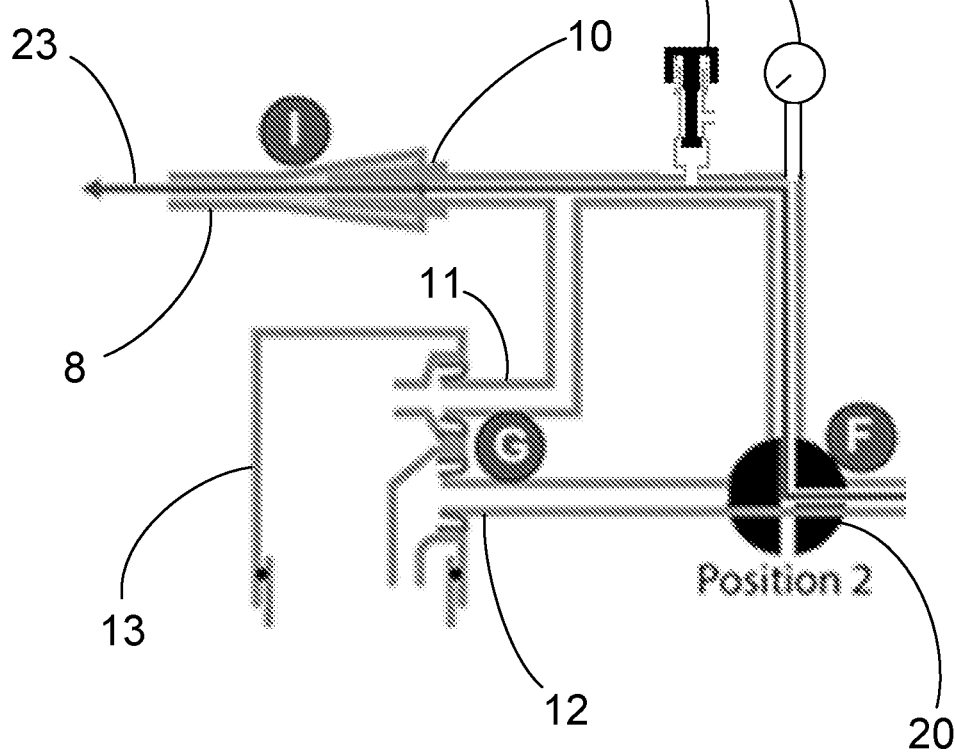

In FIGS. 4 and 5 the preferred embodiment of the valve 20 as a shunt valve is shown, but alternatively the valve 20 could be a three-way valve as shown in FIGS. 7a and 7b, or any other valve suitable for controlling the flow. The operator then presses the push-button 5 opening the valve 22, so as to open a passage through the working or suction channel 19 of the endoscope. Liquid or rather a fluid 23 comprised of air and liquid from the sampling site, e.g. in the lungs, will now be drawn through the working channel 19 to the valve 22, via the valve 22 and the connector 4 through the sampling device, out of the tubular connector 12 and into the sample container 13. In the sample container 13 the liquid will be trapped, as it falls to the bottom under the influence of gravitation, whereas the remainder 24, which is mostly air, will be sucked out through the tubular connector 11 and away via the flexible suction tube 8.

Figure 8:
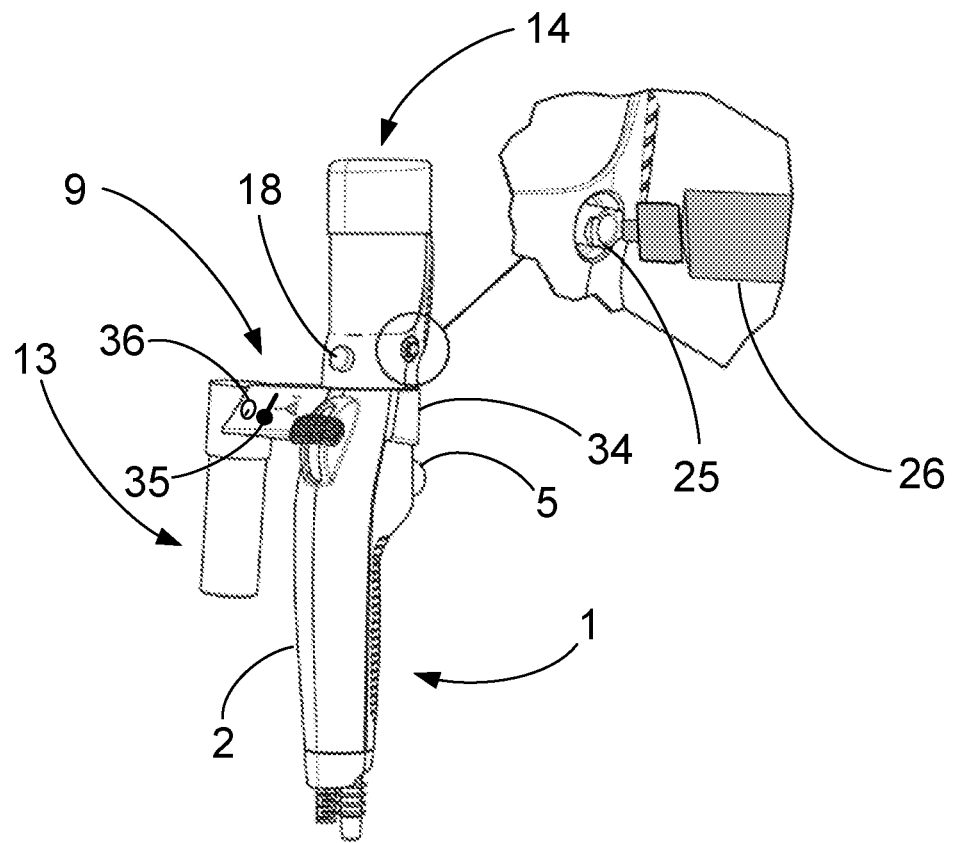
FIG. 8 shows a detail of the saline cartridge in accordance with the schematic diagram of FIG. 4, FIG. 9 schematically shows other details of the saline cartridge of FIGS. 4 and 8.
Figure 10:
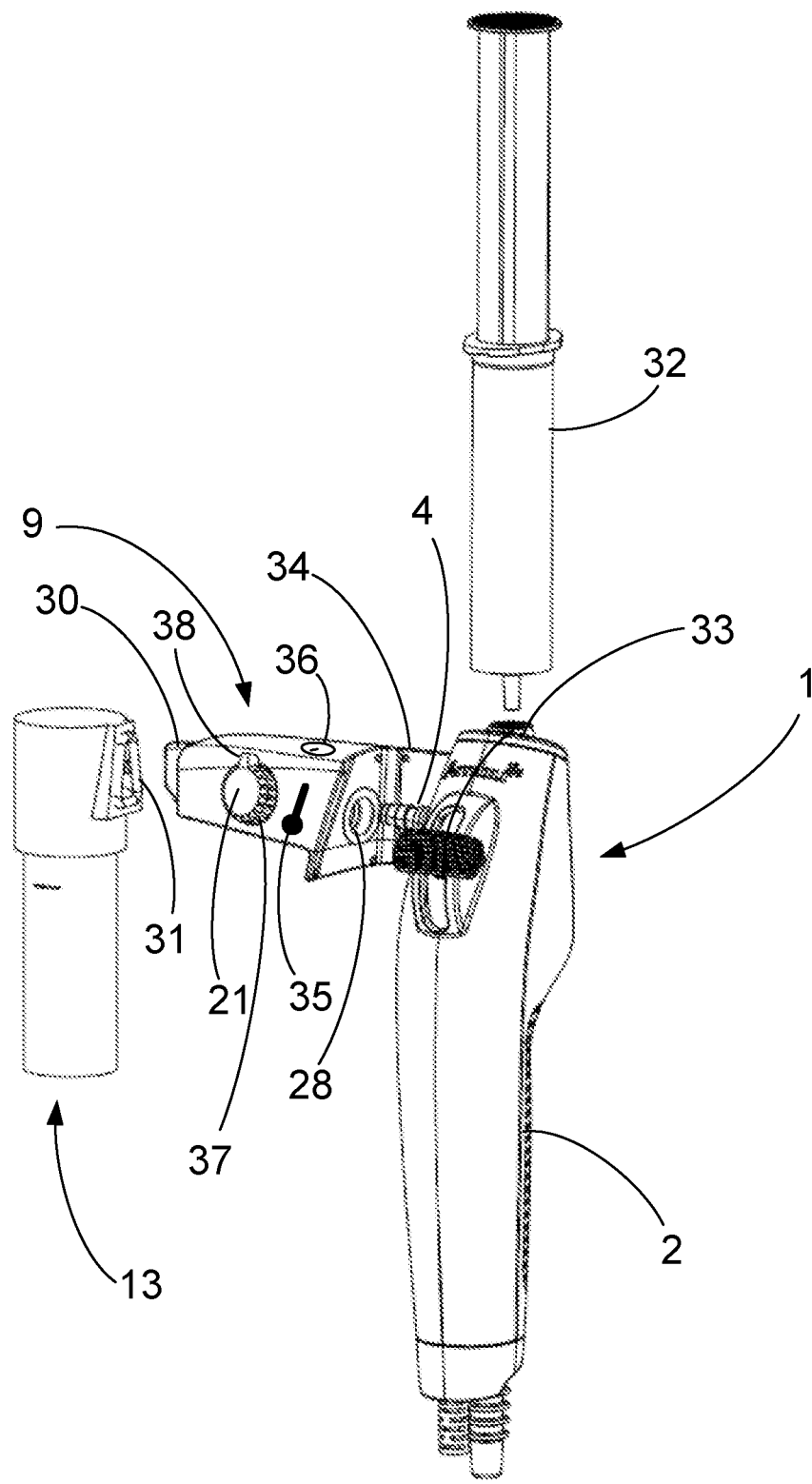
FIG. 10 shows an exploded view of an alternative embodiment of the sampling system with a sampling device according to the invention.
Figure 11:
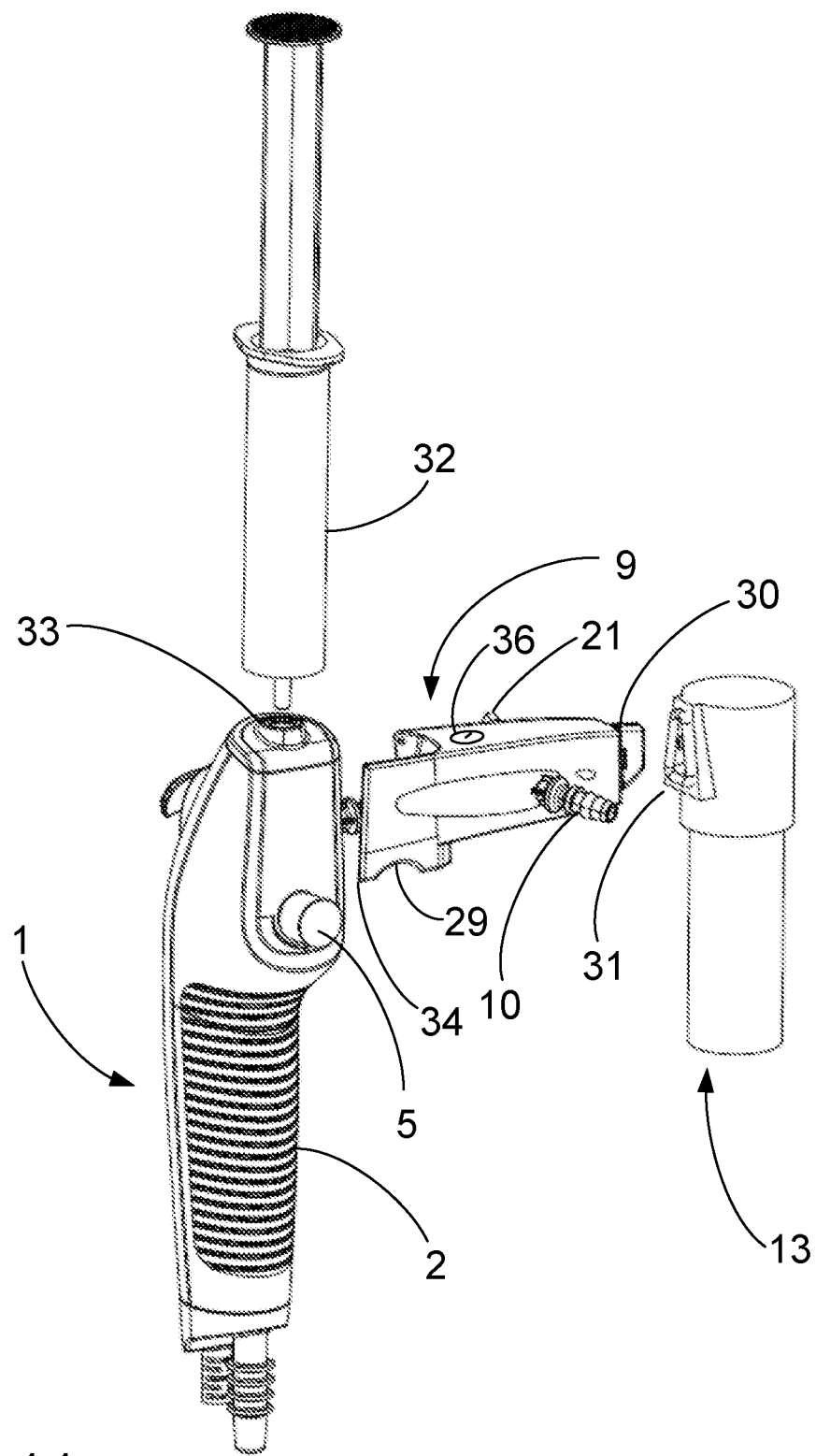
FIG. 11 shows an exploded view of the alternative embodiment of the sampling system of FIG. 10 from another angle.
Figure 12:
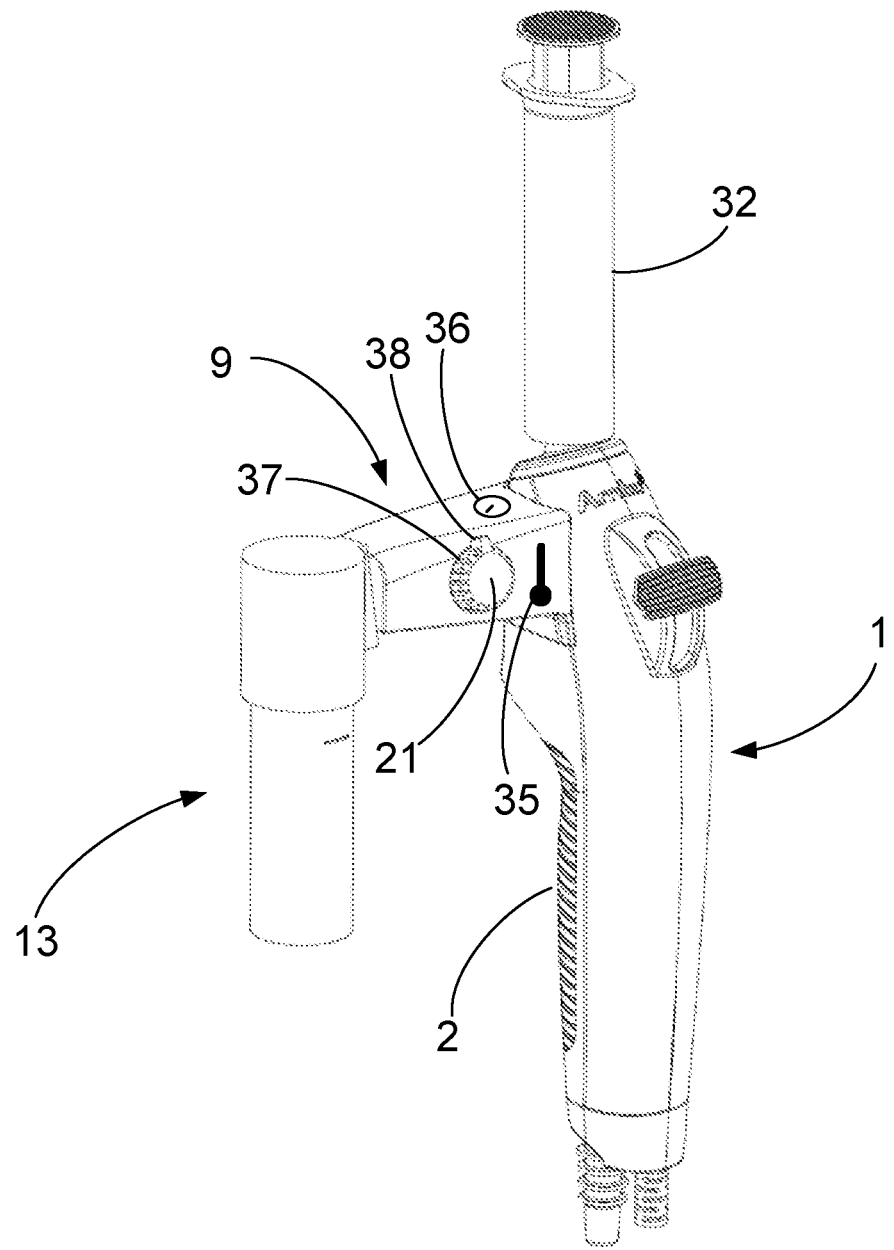
FIG. 12 shows an assembled view of the alternative embodiment of the sampling system of FIG. 10.

To better control and monitor the suction, the sampling device may optionally have a suction reduction valve 35, with which the operator can reduce the amount of suction provided by the vacuum source, and a manometer or other pressure indicator 36. The pressure indicator, if provided, is preferably located in a position on the sampling device 9 where, in use, it is visible by the operator. This could be next to the valve actuator 21 as shown in FIGS. 1, 3 and 8, or it could be in another location, e.g. the top surface, as illustrated in FIGS. 10-12. It should be noted though, that the pressure indicator 36 is just a further option, and that the suction reduction valve 35 may be implemented without the pressure indicator 36, and in principle also vice versa. The pressure indicator 36 need not be able to give a detailed reading. Rather, it is envisaged that a simple indication that the pressure is within an acceptable range may suffice.

Both the suction reduction valve 35 and the pressure indicator 36 are also schematically shown in FIGS. 4-6, 7a, 7b and 13. The actual nature and design of the suction reduction valve 35 may be one of many. It could be a throttling valve adjustable with a screw or similar. It could also be, as indicated in FIGS. 1, 3, 8 and 10-12, be a slider covering one or more openings through which false air may be drawn in to reduce the suction pressure. This could be one long opening that is gradually covered, or several smaller holes covered one by one in steps. Especially in case where false air is relied on for suction pressure reduction, the location of the suction reduction valve is preferably between the external connector 10 to the vacuum source and the tubular connector 11, in order not to draw the false air from the ambient air in the environment through the sampling container 13, as this would potentially be a cause for pollution of the sample with pollutants from the ambient environment, which were never in the lungs of the patient. Also, if the latter solution with false air is used, the pressure indicator 36 is preferably located between the suction reduction valve 35 and the tubular connector 11 order to ensure correct reading of the pressure indicator 36.

When a sample of suitable volume has accumulated in the sample container 13, the push-button 5 is released, and the valve 22 closes, as it is biased towards a closed state in a well-known manner, e.g. spring loaded.

The sample container may now be removed and possibly replaced with a new and empty one, and the process repeated.

If no more samples need be taken, the valve 20 may be turned to shunt the passage though the sample container 13 via the tubular connectors 11 and 12, corresponding to "Position 2" in FIGS. 5 and 7b. Normal suction of the fluid 23 through the working channel 19 may then be performed without having to remove the sampling device 9, i.e. normal operation with the endoscope, which may be unrelated to the sampling, may still be performed with having first to remove the sampling device 9. Furthermore, placing the valve 20 in this bypass or shunt position also allows the user to prevent any sample loss, by directing the flow directly to the wall suction, without removing the sample container from the assembly, e.g. if the user anticipates movement. By disengaging the shunt by resetting the valve 20 to position 1, the user will be able to continue sampling.

After the sampling procedure is completed the sampling device 9 may simply be disposed of. Accordingly, the sampling device 9 is adapted for single use by being manufactured entirely or at least essentially of plastic materials. That is to say low-cost materials, which need not be able to withstand a cleaning and sterilization process. So even if the endoscope 1 is not a single use endoscope 1, the sampling device 9 may well be.

If both the endoscope 1 and the sampling device 9 are adapted for single use they may be supplied as a kit of parts ready for use in the sampling procedure. This facilitates the harmonization and standardization of the sampling procedure, in turn, making it more efficient and cost efficient.

Furthermore, an opening in the sample container 13 is preferably adapted such that the distal end of the endoscope's insertion tube 3 can be entered into the sample container 13 in order to deliver a sample from e.g. the working channel 19 through the distal end of the endoscope 1. This will be relevant in the event that the working channel 19, or the channel applied for collecting a sample, is blocked e.g. by mucus, phlegm, blood etc. and the material contained in the working channel 19 is needed as a sample. Traditionally such material has been discarded by applying a pressure from the proximal end of the working channel 19, e.g. by pressing water (or air) into the working channel 19 by a connected syringe or saline container, while placing the distal end of the insertion tube 3 at a sterile cloth or paper. But in the event that it is not possible to obtain another sample, it would be an advantage if the material in the working channel 19 could be collected in a sample container 13 instead of being discarded.

This can be achieved by entering the distal end of the endoscope 1 into a sample container 13 and then applying the pressure from the proximal end of the working channel 19. The opening in the sample container 13 for this purpose could be an extra opening (not shown in figures), or it could be an existing opening also applied for the connection to the sampling device 9 through the tubular protrusions 11, 12 of the sample container connector. The opening should preferably be self-sealing to avoid spillage of sample material when the tip of the endoscope's insertion tube 3 has been removed. Also, there should be provided an opening for air pressure to escape from the sample container while the tip of the insertion tube 3 is arranged in the opening. This is to avoid that the applied pressure for removing the blockage from the working channel 19 will also remove the sample container 13 from the tip of the insertion tube 3 in the moment the blockage passes into the sample container 13.

In practice, the operator of the endoscope 1 should remove the insertion tube 3 from the body cavity and from the body as such, when a blockage of the working channel 19 is identified e.g. when suctioning is blocked. The tip of the insertion tube 3 is inserted into the suitable opening in a sample container 13, and a syringe is connected to an entrance to the working channel 19 e.g. at the handle 2 of the endoscope 1. An increasing air pressure is applied to the working channel 19 by the syringe, until the blockage is removed and the material from the working channel 19 enters into the sampling container 13. The tip of the insertion tube 3 is then removed from the sample container 13, and may be reintroduced into the body cavity if necessary.

As mentioned above there is always a risk that the operator may inadvertently orientate the sample container 13 so that the trap does not function, and the collected sample is lost to the suction source through the tubular connector 11 and flexible suction tube 8. Therefore, in addition to being adapted to extend in a well-defined manner from the endoscope 1, because of the cooperation between the receptacle 28 and the tubular connector 4, the sampling device 9 is furthermore adapted to engage the endoscope 1, in particular the handle thereof, in a manner preventing rotation about the tubular connector 4. More specifically, as can be seen from FIGS. 1 and 2, the sampling device 9 comprises a relatively rigid flange or latch member 34 adapted to the shape of the endoscope 1, but with suitable resiliency to snap into engagement with the endoscope 1 and further secure the rigid connection of the sampling device 9 against rotation with respect to the endoscope 1. Accordingly, the sampling device 9 follows the movements of the endoscope 1, or more specifically the handle 2 of the endoscope 1. Since the operator is used to gripping the handle 2 of the endoscope 1 and familiar with the orientation thereof, the likelihood that the endoscope 1 ends up in an orientation where the sample is lost, is reduced.

Figure 9:
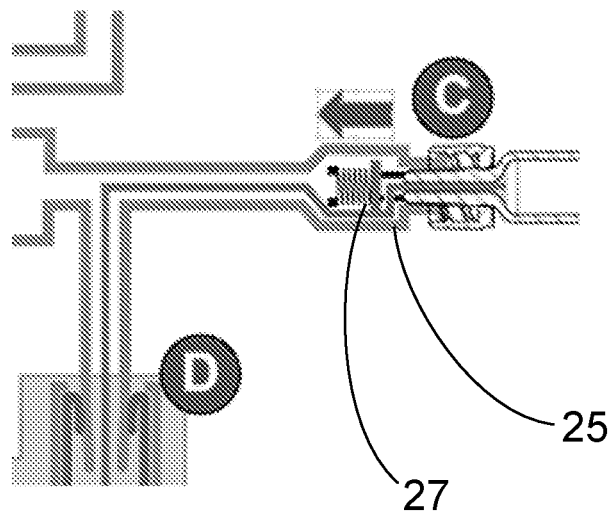

Turning now to FIG. 8 the system in the assembled state is shown with a detail of the cartridge 14 further enlarged. More specifically the cartridge 14 has an inlet 25 for injection of an additional fluid, typically but not exclusively a local anesthetic such as Lidocaine, which may be injected to reduce coughing reflexes in the patient during the procedure. This may be done by attaching a syringe 26 to the inlet 25 in a well-known manner and inject the fluid in a likewise well-known manner. As can be seen from FIG. 9 the inlet may comprise a check valve 27 closing the inlet to prevent leaking when no syringe 26 is attached, and preventing reflow into an attached syringe. The inlet is preferably a Luer lock port where the check valve 27 is actuated by the male Luer tip of the syringe 26, but other inlets may instead be used.

Turning now to FIG. 10 an alternative embodiment of a sampling system comprising component in accordance with the present invention is shown. The components largely correspond to those of the previously described embodiments, and accordingly corresponding reference numerals are used for corresponding parts. Unless otherwise stated features applied in one embodiment are likewise applicable to the other.

The endoscope 1 of which only the handle 2 is shown is identical to the one depicted in FIG. 1 but evidently sampling device 9 of the invention may be embodied in a wide range of variations suitable for different endoscopes 1 including both single use endoscopes 1 and multiple use endoscopes 1. So the endoscope 1 itself needs in no way be adapted to the sampling procedure, but can be standard endoscope 1 to which the sampling device 9 is suitably adapted. Since the sampling device 9 itself is much simpler in construction and thus cheaper to manufacture than an endoscope 1, even compared to a single use endoscope 1, a cheap and simple way of standardizing the sampling method is obtained. The sampling device 9 may comprise a flange 34 for preventing the turning of the sampling device 9 about the connector 4 when the connector is inserted in the receptacle 28. As seen in FIG. 11, the flange 34 may have a cut-out 29 adapted to accommodate the push-button 5 of the endoscope 1. This cut-out 29 may aid in retaining the sampling device 9 in good rigid engagement with the endoscope 1 and secure the position of the connector 4 in the receptacle 28.

As can further be seen from FIG. 10 the connection to the sample container comprises a generally triangular protrusion 30. The triangular protrusion comprises two channels so as to integrate the two tubular channels rather than having two separate tubular protrusions 11, 12 as in the first embodiment. The triangular shape is adapted to engage a complementary triangular receptacle 31 on the sample container 13. These complementary triangular shapes facilitate the mutual positioning of the sample container 13 and the sampling device, when attaching the sample container 13 to the sampling device 9. Furthermore, the triangular shape prevents inadvertent upside-down arrangement of the sample container. The triangular protrusion 30 may be provided with resilient latches or barbs engaging the triangular receptacle 31 or vice versa, so as to secure the engagement and prevent inadvertent separation. The same would be applicable to the tubular protrusions 11, 12 of the first embodiment.

The flow arrangement through the sampling device 9 and the sample container 13 is essentially the same as shown schematically in FIGS. 4, 5, 7a and 7b, when a flexible suction tube is connected to the connector 10, and may likewise be switched using the valve actuator 21.

Figure 13:
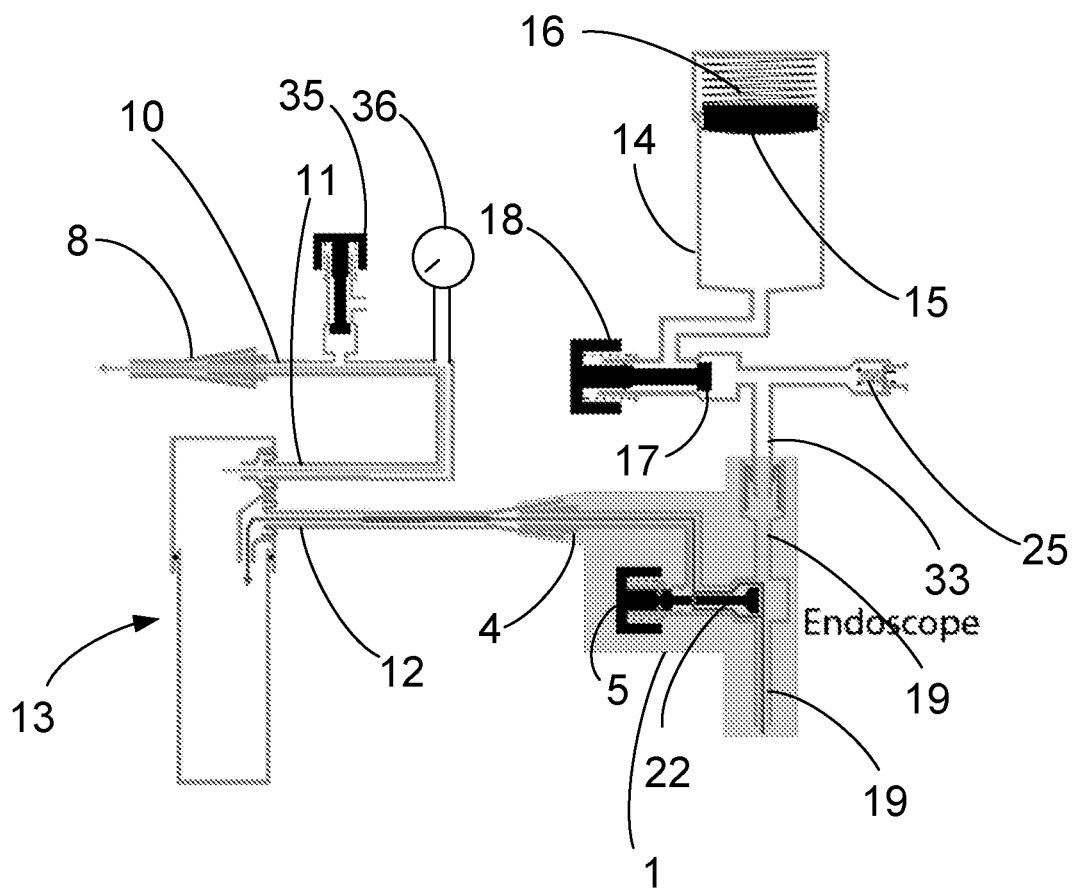
FIG. 13 shows a simplified embodiment of the sampling device according to the invention.

FIG. 13 shows a simplified embodiment of the sampling device 9 according to the invention, where the three-way valve 20 is omitted. This substantially simplifies the mechanics of the sampling device because there are essentially no movable parts, bearing in mind that the pressure indicator 36 and suction reduction valve 35 are only optional. Though, omitting the three-way valve 20 simplifies the sampling device 9, doing so will be a trade-off between practicality of the sampling procedure and the general use of the endoscope 1. More specifically, omission of the three-way valve 20 means that suction is only possible with the sample container 13 in place, or alternatively a dummy by-pass (not shown), e.g. a short U-shaped tube, arranged between the tubular protrusions 11, 12. Evidently, having to use such a dummy by-pass when the sampling container is not in place, is more complicated during a sampling procedure, than simply turning a knob functioning as the valve actuator 21.

Basically, the use of the sampling device 9 and the sample container 13 are independent on the use of the therefore optional saline cartridge 14 illustrated in FIGS. 1 to 6. A suitable size syringe 32 may instead be attached to the inlet port 33 to the working channel 19 of the endoscope 1 as shown in FIG. 12.

The skilled person will understand that the above description of the sampling device is merely an illustration of preferred embodiments, and that the sampling device may be embodied in many different ways without departing from the scope of the invention. In particular the flow paths, connectors, valves etc. may be devised in many other ways.

The invention claimed is:

1. A sampling device for the use with an endoscope having a suction channel and a suction connector in communication with said suction channel, the sampling device comprising:

an inlet adapted for connection to the suction connector of the endoscope, an outlet vacuum connector configured to be connected to a vacuum source separate from the endoscope, the vacuum source creating suction, through the outlet vacuum connector, at the inlet, and through the inlet at the suction channel of the endoscope, a container outlet adapted for connection to a sample container, and a container inlet adapted for connection to the sample container, wherein said sampling device is sized and configured to form a rigid connection with said endoscope when connected to the suction connector thereof, wherein the sampling device or the endoscope comprises a male connector and the other of the sampling device or the endoscope comprises a female connector configured to engage the male connector, the suction connector of the endoscope being either the male connector or the female connector of the endoscope;

wherein the male connector comprises a longitudinal axis and an insertion direction extends along the longitudinal axis;

wherein the sampling device is configured to engage the suction connector of the endoscope in the insertion direction to form a rigid connection therewith, and wherein the sampling device is furthermore configured to engage the sample container by insertion, in the insertion direction, of the container outlet and the container inlet into an opening of the sample container.

2. The sampling device of claim 1, wherein the female connector of the sampling device is adapted to receive the suction connector of the endoscope in said insertion direction for forming said rigid connection, and the sampling device is furthermore adapted to engage the endoscope in a manner preventing rotation around the suction connector.

3. The sampling device of claim 1, wherein the male connector of the sampling device is adapted to engage a suction connector socket of the endoscope in said insertion direction for forming said rigid connection, and the sampling device is furthermore adapted to engage the endoscope in a manner preventing rotation around the suction connector.

4. The sampling device of claim 1, wherein the sampling device comprises a valve configured to divert the suction through the sample container.

5. The sampling device of claim 4, wherein the valve comprises a valve actuator configured to change a state of the valve and divert the suction through the sampling device.

6. The sampling device of claim 5, wherein the valve actuator is sized and configured to be operated using a single finger of a hand of an operator gripping the endoscope and is located in a position on said sampling device which, when the rigid connection is formed between the sampling device and the endoscope, the valve actuator is accessible and operable by the finger of the hand of the operator.

7. The sampling device of claim 1, wherein the sampling device comprises a sample container connector adapted for connecting the sample container.

8. The sampling device of claim 7, wherein the sample container connector extends in a direction parallel to or coincident with said insertion direction.

9. The sampling device of claim 7, wherein the sample container connector is adapted to penetrate at least one seal of the sample container.

10. The sampling device of claim 7, wherein the endoscope includes an insertion tube, and wherein the opening of the sample container is adapted for receiving a distal end of the insertion tube of the endoscope.

11. The sampling device of claim 1, wherein the sampling device is adapted for single use.

12. A sampling system for the use with an endoscope, said sampling system comprising a sampling device according to claim 1 and a sample container adapted for attachment to said sampling device.

13. A method for performing a lavage, the method comprising:
providing an endoscope,
providing the sampling device of claim 1,
attaching the sampling device to the endoscope,
connecting the sampling device to a vacuum source,
inserting an insertion part of the endoscope into a body cavity,
administering a saline solution through the endoscope to the body cavity, and
collecting a sample by drawing fluid from the body cavity through the endoscope and the sampling device.

14. The sampling device of claim 1, further comprising a suction reduction valve fluidly coupled between the inlet and the outlet.

15. The sampling device of claim 14, further comprising a pressure indicator fluidly coupled between the inlet and the outlet.

16. The sampling device of claim 5, wherein the valve actuator is positioned less than 3 cm from a handle of the endoscope.

17. The sampling system of claim 12, further comprising a syringe for saline.

18. The sampling system of claim 17, wherein the syringe for saline, the sampling device, and the sample container are arranged as a kit.

19. The sampling system of claim 18, wherein the kit further comprises the endoscope.

20. The sampling system of claim 12, further comprising a saline cartridge and an endoscope, wherein the saline cartridge, the sampling device, and the sample container are arranged as a kit.

21. The sampling device of claim 1, wherein the container outlet and the container inlet comprise longitudinal protrusions that extend in parallel with the insertion direction.

22. The sampling device of claim 1, wherein the insertion direction is transverse to a longitudinal extent of a handle of the endoscope.

23. The sampling device of claim 5, wherein the valve actuator comprises a rotatable shaft having a longitudinal axis that is perpendicular to the insertion direction.

24. The sampling device of claim 1, wherein the sampling device comprises the female connector and the endoscope comprises the male connector, wherein the outlet vacuum connector is a male connector configured to receive a hose from the vacuum source which is configured to be connected to the male connector when the sampling device is not used, and wherein the outlet vacuum connector has a longitudinal axis that is not parallel to the insertion direction.

25. A sampling system for the use with an endoscope, said sampling system comprising:
the sampling device of claim 1, wherein sampling device comprises a sample container connector comprising longitudinal protrusions that extend in parallel with the insertion direction; and
the sample container, the sample container comprising a receptacle including the opening and configured to receive the longitudinal protrusions.

26. A sampling system for the use with an endoscope, said sampling system comprising:
the sampling device of claim 1, wherein sampling device comprises a triangular protrusion comprising two channels; and the sample container, the sample container comprising a complementary triangular receptacle configured to receive the triangular protrusion and the two channels.

\* \* \* \* \*